United States Patent
Koike et al.

(10) Patent No.: US 11,028,091 B2
(45) Date of Patent: Jun. 8, 2021

(54) METHOD FOR PRODUCING 3, 6-DISUBSTITUTED IMIDAZO[1, 2-B]PYRIDAZINE DERIVATIVE

(71) Applicant: DAIICHI SANKYO COMPANY, LIMITED, Tokyo (JP)

(72) Inventors: Ryoji Koike, Yokohama (JP); Yoshifumi Hachisu, Yokohama (JP); Takafumi Kitawaki, Sagamihara (JP); Shohei Shiraishi, Chigasaki (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 16/494,116

(22) PCT Filed: Mar. 13, 2018

(86) PCT No.: PCT/JP2018/009596
§ 371 (c)(1),
(2) Date: Sep. 13, 2019

(87) PCT Pub. No.: WO2018/168815
PCT Pub. Date: Sep. 20, 2018

(65) Prior Publication Data
US 2020/0062765 A1 Feb. 27, 2020

(30) Foreign Application Priority Data
Mar. 14, 2017 (JP) .............................. JP2017-049138

(51) Int. Cl.
*C07D 487/04* (2006.01)

(52) U.S. Cl.
CPC .................................. *C07D 487/04* (2013.01)

(58) Field of Classification Search
CPC ................................................. C07D 487/04
See application file for complete search history.

(56) References Cited

U.S. PATENT DOCUMENTS

| 9,187,489 B2 | 11/2015 | Takeda |
| 2014/0364413 A1 | 12/2014 | Player et al. |

FOREIGN PATENT DOCUMENTS

| JP | S60197640 | 10/1985 |
| JP | S61205220 | 9/1986 |
| JP | H08119970 | 5/1996 |
| JP | 2002193914 | 7/2002 |
| JP | 2010531342 | 9/2010 |
| JP | 2011530574 | 12/2011 |
| JP | 2015509534 | 3/2015 |
| JP | WO2013/183578 | 1/2016 |
| JP | 2016510764 | 4/2016 |

OTHER PUBLICATIONS

Extended European Search Report in EP Appln. No. 18766623.5, dated Sep. 10, 2020, 4 pages.
Akkaoui et al., "Direct Art lat ion of Imidazo [1,2-b]pyridazines: Microwave-Assisted One-Pot Suzuki Coupling/Pd-Catalyzed Acylation", European Journal of Organic Chemistry, 2010, 5:862-871.
Bendjeddou et al., "Exploration of the imidazo [1,2-b]pyridazine scaffold as a protein kinase inhibitor" European Journal of Medical Chemistry, 2017, 125:696-709.
PCT International Search Report and Written Opinion in International Appln. No. PCT/JP2018/009596, dated Jun. 5, 2018, 9 pages with English Translation.
Indian Office Action in IN Appln. No. 201917038488, dated Mar. 31, 2021, 7 pages.

*Primary Examiner* — Brian E McDowell
(74) *Attorney, Agent, or Firm* — Fish & Richardson P.C.

(57) ABSTRACT

Provided is a novel and industrially useful method for producing a 3, 6-disubstituted imidazo[1, 2-b]pyridazine derivative. The present invention provides a method for producing a 3, 6-disubstituted imidazo[1, 2-b]pyridazine derivative, which uses 6-fluoroimidazo[1, 2-b]pyridazine as a starting material, while using an aromatic substitution reaction that utilizes C—H activation by means of palladium.

5 Claims, 1 Drawing Sheet

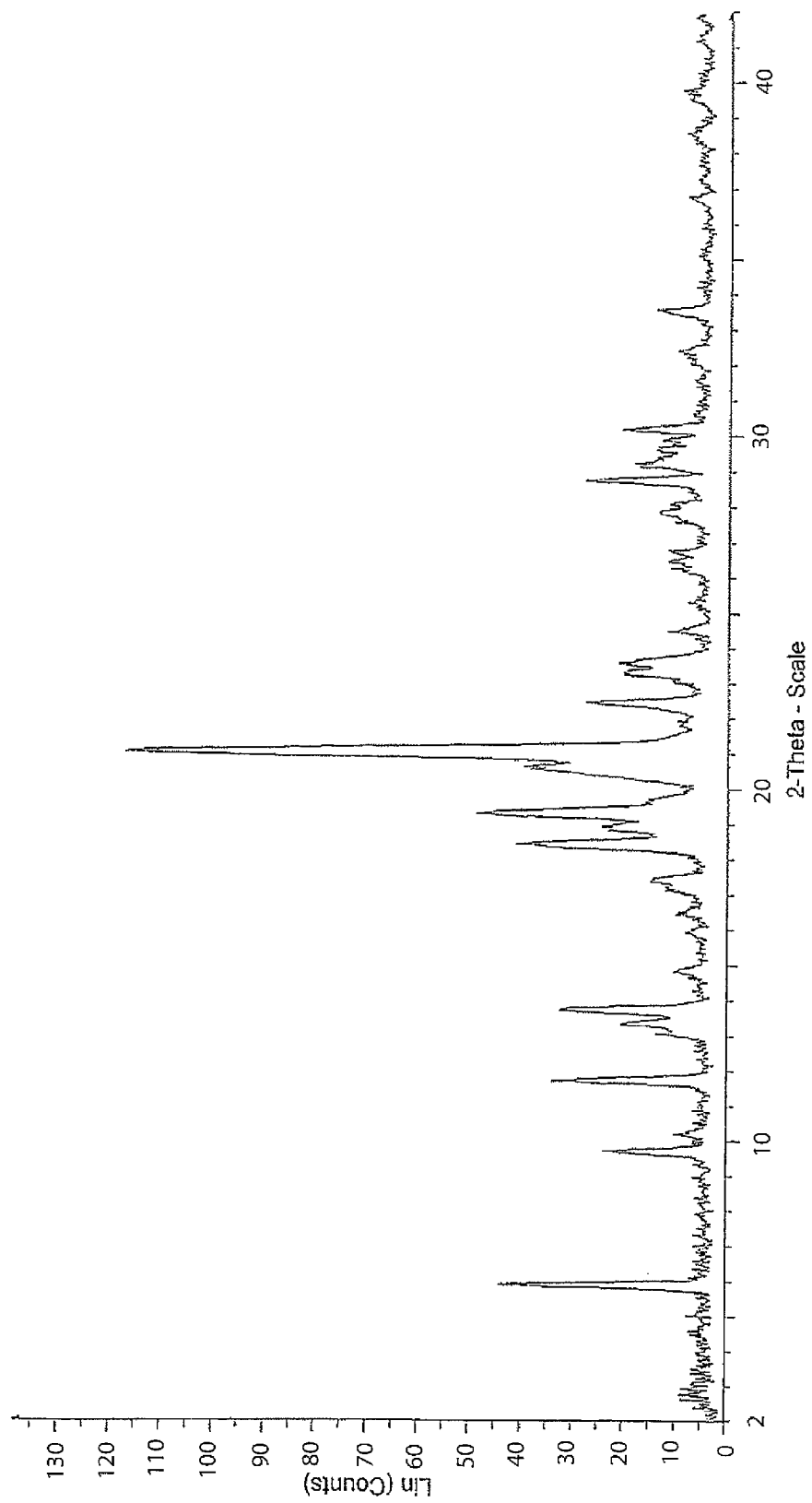

METHOD FOR PRODUCING 3,6-DISUBSTITUTED IMIDAZO[1,2-B]PYRIDAZINE DERIVATIVE

CROSS-REFERENCE TO RELATED APPLICATIONS

This application is a national stage application under 35 U.S.C. § 371 of International Patent Application No. PCT/JP2018/009596, filed on Mar. 13, 2018, which claims priority from Japanese Patent Application No. JP 2017-049138, filed on Mar. 14, 2017. The disclosures of those applications are incorporated by reference herein in their entirety.

TECHNICAL FIELD

The present invention relates to a novel method for producing a 3,6-disubstituted-imidazo[1,2-b]pyridazine derivative.

BACKGROUND ART

It is known that a 3,6-disubstituted-imidazo[1,2-b]pyridazine derivative is useful as a medicament or a raw material for producing the same, and is also useful for the treatment of tumor (Patent Literature 1).

In Patent Literature 1, all 3,6-disubstituted-imidazo[1,2-b]pyridazine derivatives are synthesized by introducing a substituent into position 6 of 3-bromo-6-chloroimidazo[1,2-b]pyridazine used as a starting material using an aromatic nucleophilic substitution reaction, and subsequently introducing a substituent into position 3 thereof using a Suzuki-Miyaura coupling reaction (Patent Literature 1, for example, Example 21).

Moreover, as another method for synthesizing a 3,6-disubstituted-imidazo[1,2-b]pyridazine derivative, there is known a method which comprises introducing an aryl group into position 3 of 6-chloroimidazo[1,2-b]pyridazine used as a starting material using an aromatic substitution reaction utilizing C—H activation catalyzed by palladium (Non Patent Literature 1).

The synthesis method of Patent Literature 1 has the following restriction: a halogen atom is essential for the reactive site of the Suzuki-Miyaura coupling reaction on the imidazo[1,2-b]pyridazine ring. On the other hand, the synthesis method of Non Patent Literature 1 is disadvantageous in that a large amount of a palladium catalyst is required, and also in that when an electron-donating substituent is present on the aryl group to be introduced, the yield becomes moderate (Non Patent Literature 1, for example, Table 2 Entry 11).

CITATION LIST

Patent Literature

Patent Literature 1: WO2013-183578

Non Patent Literature

Non Patent Literature 1: Eur. J. Org. Chem., 862-871 (2010)

SUMMARY OF INVENTION

Technical Problem

The present invention provides a method for producing a 3,6-disubstituted-imidazo[1,2-b]pyridazine derivative using an aromatic substitution reaction utilizing C—H activation catalyzed by palladium, using 6-fluoroimidazo[1,2-b]pyridazine as a starting material, wherein the method is an industrially useful novel method where the amount of a palladium catalyst used is small and an aryl group having an electron-donating substituent with a complicated structure can be introduced with a high yield.

Solution to Problem

The present invention relates to the following (1) to (7).
(1) A method for producing a compound represented by formula (III) or a salt thereof:

[Formula 3]

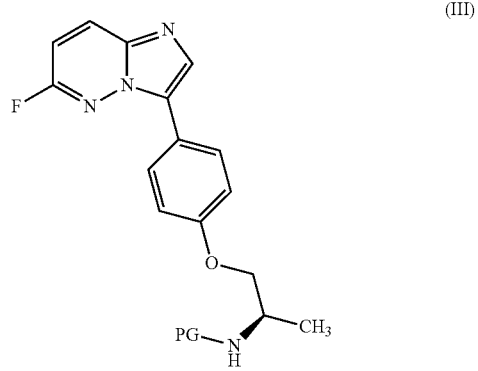

wherein PG represents a protecting group for a nitrogen atom,
the method comprising reacting a compound represented by formula (I) or a salt thereof:

[Formula 1]

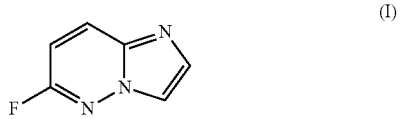

with a compound represented by formula (II) or a salt thereof:

[Formula 2]

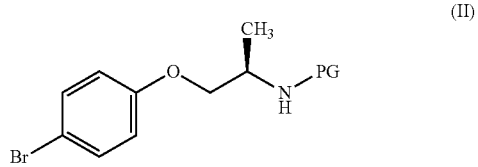

wherein each symbol is as defined above,
in a solvent in the presence of a palladium catalyst and a base.
(2) The method according to the above (1), wherein in the formulas (II) and (III), PG is a tert-butoxycarbonyl group.
(3) The method according to the above (1) or (2), wherein the palladium catalyst consists of palladium acetate and tris(2-methylphenyl)phosphine.

(4) The method according to any one of the above (1) to (3), wherein the base is potassium carbonate.

(5) The method according to any one of the above (1) to (4), wherein the solvent is diethylene glycol dimethyl ether.

(6) A method for producing a compound represented by formula (V) or a salt thereof:

[Formula 5]

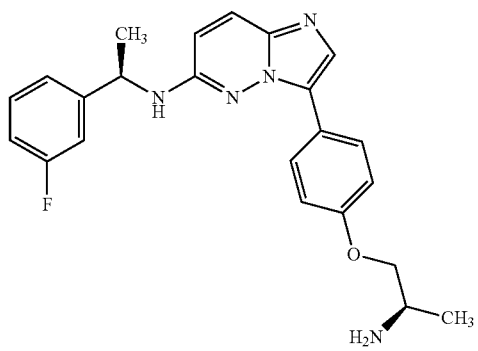

(V)

the method comprising:

a step of reacting the compound represented by the formula (III) produced by the method according to any one of the above (1) to (5) or a salt thereof with a compound represented by formula (IV) or a salt thereof:

[Formula 4]

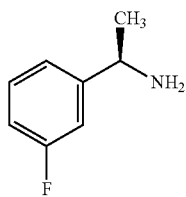

(IV)

and a step of deprotecting PG on the nitrogen atom.

(7) A method for producing an adipate of the compound represented by the formula (V) produced using the method described in the above (6), which comprises forming a salt of the compound represented by the formula (V) using adipic acid.

In the present invention, the "palladium catalyst" is a divalent palladium catalyst or a zero-valent palladium catalyst. Examples thereof include [tris(2-methylphenyl)phosphine]palladium(0).

The "palladium catalyst" of the present invention includes a catalyst prepared in a reaction system by, for example, allowing a monodentate phosphine ligand such as triphenylphosphine, tri-t-butylphosphine, or tris(2-methylphenyl)phosphine, or a bidentate phosphine ligand such as 1,1-bis(diphenylphosphino)methane or 1,2-bis(diphenylphosphino)ethane, to act on a palladium compound such as palladium chloride or palladium acetate.

In the present invention, the reaction can be carried out using a very small amount of a palladium catalyst. The amount of the palladium catalyst used is preferably 0.5 to 10 mol %, and more preferably 1 to 5 mol %, based on the amount of the compound of the formula (I). The amount of the palladium catalyst used is further preferably 2 mol %.

The protecting group (PG) for the nitrogen atom which can be used in the present invention is not particularly limited, as long as it is a substituent that reduces the reactivity of the nitrogen atom to an electrophilic addition reaction. For example, the protecting groups disclosed in Protective Groups in Organic Synthesis (T. W. Green and P. G. M. Wuts, John Wiley & Sons, Inc., New York, 1991) can be used. The protecting group is preferably a tert-butoxycarbonyl group or a benzyloxycarbonyl group.

The solvent which can be used in the present invention is not particularly limited, as long as it does not inhibit the aromatic substitution reaction involving a C—H activation reaction catalyzed by palladium. Examples thereof include toluene, cyclopentyl methyl ether, 1,4-dioxane, and diethylene glycol dimethyl ether. The solvent is preferably a solvent miscible with water, and examples thereof include diethylene glycol dimethyl ether.

The compound represented by the formula (III) and the compound represented by the formula (V) according to the present invention can be each converted to a salt by reacting the compounds with an acid.

Examples of the salt include: inorganic acid salts including hydrohalides such as a hydrofluoride, a hydrochloride, a hydrobromide, or a hydroiodide, a nitrate, a perchlorate, a sulfate, and a phosphate; organic acid salts including $C_1$-$C_6$ alkylsulfonates such as a methanesulfonate, a trifluoromethanesulfonate, or an ethanesulfonate, arylsulfonates such as a benzenesulfonate or a p-toluenesulfonate, an acetate, a malate, a fumarate, a succinate, a citrate, an ascorbate, a tartrate, an oxalate, and an adipate; and amino acid salts such as a glycine salt, a lysine salt, an arginine salt, an ornithine salt, a glutamate, and an aspartate.

When the compound represented by the formula (III) or a salt thereof and the compound represented by the formula (V) or a salt thereof according to the present invention are left in the atmosphere or are recrystallized, these compounds incorporate water molecules and become hydrates in some cases. Such hydrates are also included in the present invention.

When the compound represented by the formula (III) or a salt thereof and the compound represented by the formula (V) or a salt thereof according to the present invention are left in a solvent or are recrystallized, these compounds absorb a certain type of solvent and become solvates in some cases. Such solvates are also included in the present invention.

Advantageous Effects of Invention

The present invention can provide a method for producing a 3,6-disubstituted-imidazo[1,2-b]pyridazine derivative using an aromatic substitution reaction utilizing C—H activation catalyzed by palladium, using 6-fluoroimidazo[1,2-b]pyridazine as a starting material, wherein the method is an industrially useful novel method where the amount of a palladium catalyst used is small and an aryl group having an electron-donating substituent with a complicated structure can be introduced with a high yield.

DESCRIPTION OF EMBODIMENTS

The present invention will be described below. The reaction conditions of the present invention should not be interpreted as being limited thereto. In the present invention, there is a case where a functional group of a compound is protected by a suitable protecting group. Examples of such a functional group include a hydroxyl group, a carboxy group, and an amino group. With regard to the types of protecting groups and conditions for the introduction and removal of such protecting groups, those described in Protective Groups in Organic Synthesis (T. W. Green and P. G. M. Wuts, John Wiley & Sons, Inc., New York, 1991) can be referred to.

BRIEF DESCRIPTION OF DRAWING

FIG. 1 shows a powder X-ray diffraction pattern of the crystals of compound (6) obtained in Example 7. The vertical axis indicates the diffraction intensity as a relative line intensity (counts), and the horizontal axis indicates values of the diffraction angle 2θ.

EXAMPLES

Hereinafter, the present invention will be described in more detail with reference to the following Examples. However, these Examples are not intended to limit the scope of the present invention.

It is to be noted that abbreviations used in the Examples have the following meanings.

g: gram, mL: milliliter, L: liter, MHz: megahertz.

In the following Examples, with regard to the nuclear magnetic resonance (hereinafter referred to as $^1$H NMR: 400 MHz) spectrum, the chemical shift value was provided as a δ value (ppm), using tetramethylsilane as a standard substance. For the splitting pattern, the following symbols were used: s, singlet; d, doublet; dd, double doublet; m, multiplet; and br, broad.

In addition, the powder X-ray diffraction analysis apparatus and analysis conditions were as follows.

Apparatus: D8 Discover with GADDS CST, manufactured by Bruker Axs
X-ray source: CuKα λ=1.54 angstroms
Method: reflection method
Tube voltage: 40 kV
Tube current: 40 mA
Scanning range: 2° to 42°
Scanning rate: 10°/min Example 1 tert-Butyl [(2R)-1-(4-bromophenoxy)propan-2-yl] carbamate (1)

[Formula 6]

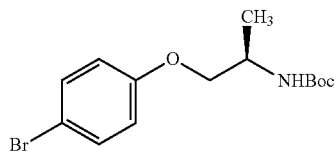

(1)

Under the nitrogen atmosphere, 1-bromo-4-fluorobenzene (100 g, 0.57 mol, 1 equiv.), N-methylpyrrolidone (500 mL), and D-alaninol (51.5 g, 0.69 mol, 1.2 equiv.) were added, and then potassium tert-butoxide (96.1 g, 0.86 mol, 1.5 equiv.) was added thereto at 40° C. or less. The resulting mixture was stirred at an internal temperature of about 65° C. for 3 hours and cooled to 20° C. or less. After that, isopropyl acetate (500 mL) and water (1000 mL) were added thereto, and the resulting mixture was stirred. After standing and separating, the aqueous layer was extracted twice with isopropyl acetate (500 mL), and all the organic layers were combined. The combined organic layer was washed twice with water (500 mL), and the obtained organic layer was concentrated under reduced pressure to 300 mL. The operation of further adding ethanol (1000 mL) thereto and concentrating the obtained mixture under reduced pressure to 300 mL was repeated twice. To this solution, tetrahydrofuran (200 mL) was added, and the resulting mixture was cooled to 5° C. or less. tert-Butyl dicarbonate (162 g, 0.74 mol, 1.3 equiv.) was dissolved in tetrahydrofuran (100 mL), and the resulting solution was added dropwise to the mixture at 6° C. or less over about 2 hours. The resulting mixture was stirred at 5° C. or less for 1 hour, and then raised to about 20° C. and stirred overnight. Ethanol (230 mL) was added thereto, and then water (800 mL) was added dropwise over 1.5 hours. The resulting mixture was stirred at about 50° C. for 1 or more hours, and then gradually cooled to 25° C., and stirred overnight. The precipitated solid was filtered and washed with a mixed solution of ethanol (230 mL) and water (270 mL). The solid was dried under vacuum at an external temperature of 40° C. to obtain the title compound (1) (170 g).

Example 2

6-Fluoroimidazo[1,2-b]pyridazine methanesulfonate (2)

[Formula 7]

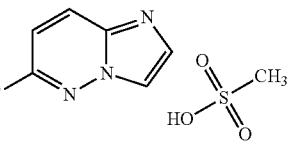

(2)

Under the nitrogen atmosphere, benzyltriethylammonium chloride (445 g, 1.95 mol, 1 equiv.) and 6-chloroimidazo[1,2-b]pyridazine (300 g, 1.95 mol, 1 equiv.) (available from Combi-Block or the like) were successively added to dimethyl sulfoxide (1500 mL). Cesium fluoride (534 g, 3.51 mol, 1.8 equiv.) was further added thereto, and then the resulting mixture was stirred at an internal temperature of 79° C. to 81° C. for 4 hours. The mixture was cooled to room temperature, toluene (1500 mL) and sodium bicarbonate (48 g, 0.59 mol, 0.3 equiv.) were added to the mixture, and then water (1500 mL) was added thereto. Acetonitrile (600 mL) was added to the mixture, the resulting mixture was stirred, and then the organic layer and the aqueous layer were separated. Furthermore, the operation of extracting this aqueous layer with a mixed solution of toluene (1500 mL) and acetonitrile (300 mL) was repeated three times, and all the organic layers were combined. The combined organic layer was concentrated under reduced pressure to adjust the liquid volume to 2400 mL. Activated carbon (30 g) moistened with toluene (150 mL) was added thereto. The resulting mixture was stirred around 25° C. for 1 hour, and then filtered and washed with toluene (750 mL). Acetonitrile (900 mL) was added thereto, and then methanesulfonic acid (188 g, 1.95 mol, 1 equiv.) was added dropwise at an internal temperature of 22° C. to 37° C. over 1 hour. The resulting mixture was stirred at 27° C. to 31° C. for 1.5 hours, and then the precipitated solid was filtered and washed with toluene (900 mL). The solid was dried under reduced pressure at an external temperature of 40° C. for 5 hours to obtain the title compound (2) (396.9 g).

Example 3 tert-Butyl {(2R)-1-[4-(6-fluoroimidazo[1,2-b]pyridazin-3-yl)phenoxy]propan-2-yl}carbamate (3)

[Formula 8]

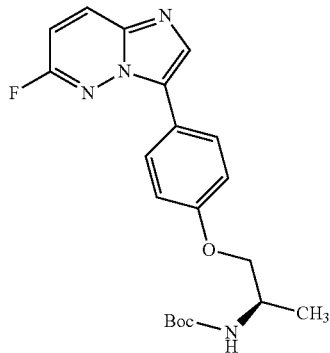

(3)

Under the nitrogen atmosphere, methyl tert-butyl ether (12 L), water (2.6 L), potassium carbonate (691 g, 5.0 mol, 1.1 equiv.), and the compound of the formula (2) (1.17 kg, 5.0 mol, 1.1 equiv.) were successively added. The resulting mixture was stirred at an internal temperature of 19° C. for 5 minutes and allowed to stand, and then the aqueous layer was discharged. The obtained organic layer was concentrated under reduced pressure to adjust the liquid volume to 7.5 L. Diethylene glycol dimethyl ether (7.5 L) was added thereto, and the resulting mixture was concentrated under reduced pressure again to adjust the liquid volume to 8.25 L. To this solution, the compound of the formula (1) (1.5 kg, 4.54 mol, 1 equiv.), tris(2-methylphenyl)phosphine (27.7 g, 0.09 mol, 0.02 equiv.), potassium carbonate (1.26 kg, 9.12 mol), and palladium acetate (20.4 g, 0.09 mol, 0.02 equiv.) were successively added, followed by washing with diethylene glycol dimethyl ether (0.3 L). The resulting mixture was stirred at an internal temperature of 95° C. to 108° C. for 9 hours and then stirred at an internal temperature of 58° C. to 61° C. for 11 hours. Purified water (7.5 L) was added thereto, and the resulting mixture was warmed to an internal temperature of 71° C., and then the aqueous layer was discharged. To the organic layer, 1-methylimidazole (1.5 L) was added, and the resulting mixture was cooled. The mixture was stirred at 25° C. to 30° C. for 40 minutes, and then water (9 L) was intermittently added thereto at an internal temperature of 25° C. to 29° C. over 1.5 hours. The resulting mixture was stirred around 25° C. for 19 hours, and then crystals were filtered and washed with a mixed solution of diethylene glycol dimethyl ether (3 L) and water (3 L) and then with water (3 L). The obtained solid was dried under reduced pressure at an external temperature of 40° C. to obtain the title compound (3) (1.65 kg, 94.1% (gross weight)).

$^{1}$HNMR (500 MHz, CDCl$_3$): δ=1.32 (d, J=7.0 Hz, 3H), 1.47 (s, 9H), 4.00 (d, J=4.0 Hz, 2H), 4.10 (brs, 1H), 4.80 (brs, 1H), 6.87 (d, J=7.6 Hz, 1H), 7.02-7.08 (m, 2H), 7.92-7.97 (m, 2H), 8.00 (s, 1H), 8.06 (dd, J=7.6, 6.0 Hz, 1H)

Example 4 tert-Butyl {(2R)-1-[4-(6-{[(1R)-1-(3-fluorophenyl)ethyl]amino}imidazo[1,2-b]pyridazin-3-yl)phenoxy]propan-2-yl}carbamate hydrochloride (4)

[Formula 9]

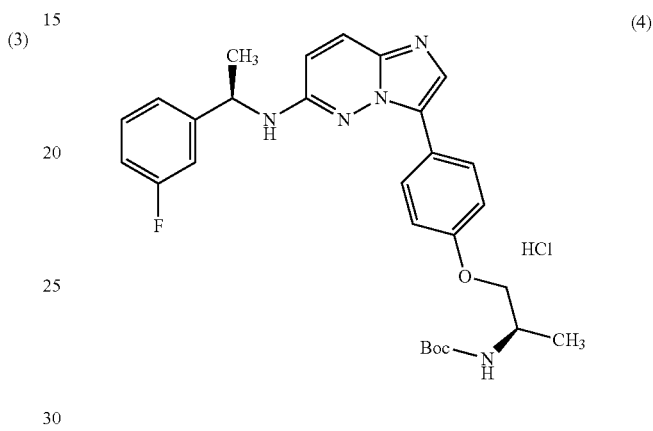

(4)

Under the nitrogen atmosphere, (1R)-1-(3-fluorophenyl)ethanamine (400 g, 2.87 mol, 1 equiv.), trisodium phosphate (471 g, 2.87 mol, 1 equiv.), and the compound of the formula (3) (1.22 kg (net weight: 1.12 kg), 3.16 mol, 1.1 equiv.) were successively added to dimethyl sulfoxide (2.4 L). This mixed solution was warmed, and stirred at an internal temperature of 95° C. to 99° C. for 55 hours. The solution was cooled, and cyclopentyl methyl ether (4 L) and water (8 L) were added thereto at an internal temperature of 24° C. The resulting mixture was warmed to 50° C., and the aqueous layer was discharged. After that, water (4 L) was added to the organic layer remaining, and the aqueous layer was discharged again. The obtained organic layer was concentrated under reduced pressure to adjust the liquid volume to 4 L. The liquid was filtered using cyclopentyl methyl ether (0.4 L).

A portion of the obtained solution in an amount equal to ⅝ times the amount thereof was taken out thereof and used in the subsequent reaction. To the solution, cyclopentyl methyl ether (0.25 L), tetrahydrofuran (3 L), and water (0.05 L) were successively added, and concentrated hydrochloric acid (74.9 g, 1.15 mol, 0.4 equiv.) was added thereto at an internal temperature of 23° C. The resulting mixture was stirred at 25° C. for 1.5 hours, and then a mixed solution of cyclopentyl methyl ether (1.5 L) and tetrahydrofuran (1.5 L) was added thereto. The resulting mixture was further stirred for 1.5 hours, and then concentrated hydrochloric acid (112 g, 1.72 mol, 0.6 equiv.) was added thereto in three portions every hour. The resulting mixture was stirred at an internal temperature of 25° C. for 18 hours. The precipitated solid was filtered and washed with a mixed solution of cyclopentyl methyl ether (1.25 L), tetrahydrofuran (1.25 L), and water (0.025 L). The solid was dried under reduced pressure at an external temperature of 40° C. to obtain the title compound (4) (808.0 g).

Example 5

3-{4-[(2R)-2-Aminopropoxy]phenyl}-N-[(1R)-1-(3-fluorophenyl)ethylimidazo[1,2-b]pyridazin-6-amine dihydrochloride (5)

[Formula 10]

(5)

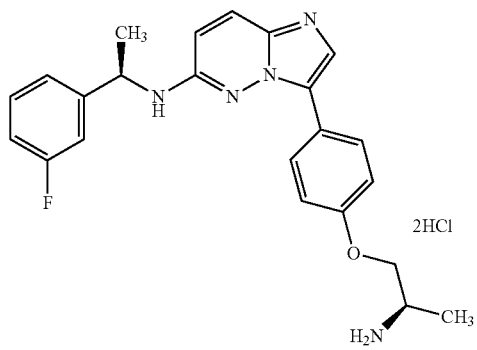

2HCl

Under the nitrogen atmosphere, the compound of the formula (4) (120.0 g) was dissolved in ethanol (1080 mL), and then activated carbon (12 g) moistened with ethanol (60 mL) was added thereto. The resulting mixture was stirred for 1 hour, and then filtered and washed with ethanol (120 mL). To the obtained solution, concentrated hydrochloric acid (43.3 g) was added, and the resulting mixture was warmed, and stirred at 65° C. to 70° C. for 4 hours. The mixture was cooled to an internal temperature of 20° C. over 2 hours and stirred at that temperature for 1 hour, and then further cooled to 1° C. over 1 hour. The mixture was stirred at an internal temperature of −1° C. to 1° C. for 19.5 hours. After that, the precipitated solid was filtered and washed with a mixed solution of cold ethanol (240 mL) and water (6 mL). The solid was dried under reduced pressure at an external temperature of 40° C. to obtain the title compound (5) (100.5 g).

Example 6

3-{4-[(2R)-2-Aminopropoxy]phenyl}-N-[(1R)-1-(3-fluorophenyl)ethylimidazo[1,2-b]pyridazin-6-amine (V)

Under the nitrogen atmosphere, the compound of the formula (5) (75.5 g, 0.17 mol), ethanol (604 mL), and water (604 mL) were mixed together and then warmed to an internal temperature of 50° C. to dissolve the compound. A 25% sodium hydroxide aqueous solution (68.1 g) was added thereto at an internal temperature of 50° C. for 3 minutes. After that, the resulting mixture was cooled to an internal temperature of 1° C. over 1.5 hours and stirred for 18.5 hours. The precipitated solid was filtered and washed with a cold mixed solution of ethanol (151 mL) and water (151 mL). The solid was dried under reduced pressure at an external temperature of 40° C. to obtain the title compound (V) (58.8 g).

Example 7

3-{4-[(2R)-2-Aminopropoxy]phenyl}-N-[(1R)-1-(3-fluorophenyl)ethylimidazo[1,2-b]pyridazin-6-amine adipate (6)

[Formula 11]

(6)

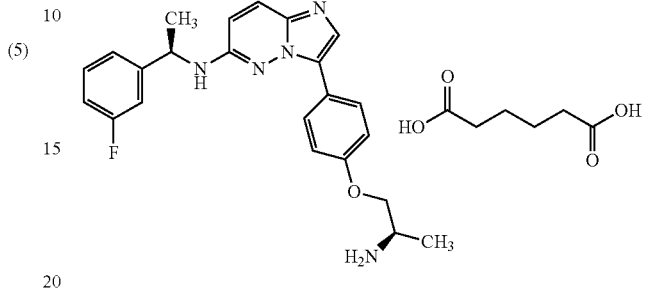

Under the nitrogen atmosphere, ethanol (90 mL) was added to the compound of the formula (V) (30.0 g, 1 equiv.), and the temperature was raised to 50° C. to dissolve the compound, followed by filtration. Adipic acid (11.4 g, 1.1 equiv.) was dissolved in a mixed solution of ethanol (75 mL) and water (75 mL), followed by filtration. The filtrate was added to a 3-{4-[(2R)-2-aminopropoxy]phenyl}-N-[(1R)-1-(3-fluorophenyl)ethylimidazo[1,2-b] pyridazin-6-amine solution. Water (54 mL) was added thereto and 30.0 mg (0.1% by weight) of seed crystals* were added thereto at an internal temperature of 27° C., followed by stirring for 18 hours. Water (306 mL) was added thereto at an internal temperature of about 41° C. over 1.3 hours, and then the resulting mixture was stirred for 2 hours. Furthermore, the mixture was cooled to an internal temperature of −1° C. over 1.5 hours and stirred for 16.5 hours. Crystals were filtered and washed with a cold mixed solution of ethanol (18 mL) and water (42 mL). The crystals were dried under reduced pressure at an external temperature of 40° C. to obtain crystals of the title compound (6) (37.2 g). An XRD chart of the obtained crystals is shown in FIG. 1.

*Crystals precipitate spontaneously when the reaction solution is stirred for a long period of time. Here, however, in order to reduce the time taken for crystals to precipitate, crystals previously obtained in a similar experiment were added as seed crystals.

Reference Example tert-Butyl {(2R)-1-[4-(6-chloroimidazo[1,2-b]pyridazin-3-yl)phenoxy]propan-2-yl}carbamate (7)

[Formula 12]

(7)

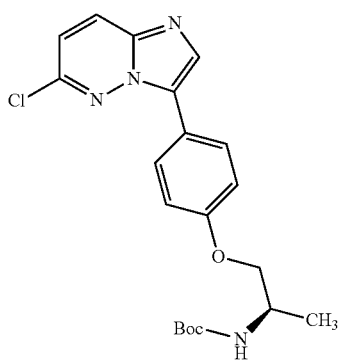

6-Chloroimidazo[1,2-b]pyridazine and the compound of the formula (1) were reacted under the conditions disclosed in Non Patent Literature 1 (palladium acetate, 0.1 equiv.; triphenylphosphine, 0.2 equiv.; potassium carbonate, 2 equiv.; toluene, 110®C; 24 hours). As a result, the reaction rate of the compound of the formula (7) on HPLC was about 1.4%.

Contrary to the disclosure in Non Patent Literature 1, it was revealed that when 6-chloroimidazo[1,2-b]pyridazine was used as a starting material, the introduction of an aryl group having an electron-donating substituent with a complicated structure causes an extremely large reduction in yield. In contrast, in Example 3 using 6-fluoroimidazo[1,2-b]pyridazine as a starting material, a high reaction rate was exhibited although the amount of the palladium catalyst used was one fifth of that in the Reference Example, and this shows an excellent effect of the present invention.

The invention claimed is:

1. A method for producing a compound represented by Formula (III) or a salt thereof:

[Formula III]

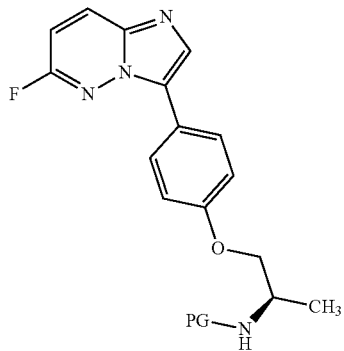

(III)

wherein PG represents a protecting group for a nitrogen atom, the method comprising reacting a compound represented by Formula (I) or a salt thereof:

[Formula I]

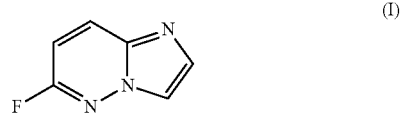

(I)

with a compound represented by Formula (II) or a salt thereof:

[Formula II]

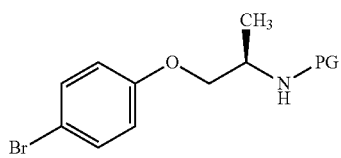

(II)

wherein each symbol is as defined above, in a solvent in the presence of a palladium catalyst and a base.

2. The method according to claim 1, wherein in Formulae (II) and (III), PG is a tert-butoxycarbonyl group.

3. The method according to claim 1, wherein the palladium catalyst consists of palladium acetate and tris(2-methylphenyl)phosphine.

4. The method according to claim 1, wherein the base is potassium carbonate.

5. The method according to claim 1, wherein the solvent is diethylene glycol dimethyl ether.

* * * * *